United States Patent [19]
Rossen et al.

[11] Patent Number: 5,823,186
[45] Date of Patent: Oct. 20, 1998

[54] RESPIRATOR

[75] Inventors: Thomas Rossen; Dieter Sahmkow, both of Lübeck, Germany

[73] Assignee: Drägerwerk AG, Lübeck, Germany

[21] Appl. No.: 796,516

[22] Filed: Feb. 6, 1997

[30] Foreign Application Priority Data

Jun. 20, 1996 [DE] Germany .................. 196 24 561.3

[51] Int. Cl.⁶ ................................. A61M 16/00
[52] U.S. Cl. .................. 128/204.21; 128/204.18; 128/203.12; 128/205.11
[58] Field of Search ............. 128/204.21, 204.18, 128/208.12, 208.14, 203.25, 204.24, 205.11

[56] References Cited

U.S. PATENT DOCUMENTS

| | | | |
|---|---|---|---|
| 3,435,822 | 4/1969 | Ziermann et al. | 128/204.24 |
| 3,863,630 | 2/1975 | Cavallo . | |
| 4,186,737 | 2/1980 | Valenta et al. | 128/204.24 |
| 4,197,842 | 4/1980 | Anderson | 128/203.12 |
| 4,313,436 | 2/1982 | Schwanbom et al. | 128/208.19 |
| 5,161,525 | 11/1992 | Kimm et al. | 128/204.26 |
| 5,211,170 | 5/1993 | Press | 128/204.18 |
| 5,239,994 | 8/1993 | Atkins | 128/204.18 |
| 5,452,714 | 9/1995 | Anderson et al. | 128/205.11 |
| 5,615,669 | 4/1997 | Olsson et al. | 128/203.25 |

FOREIGN PATENT DOCUMENTS

| | | | |
|---|---|---|---|
| 2036184 | 9/1991 | Canada | A61M 16/00 |
| 0 343 542 | 11/1989 | European Pat. Off. . | |
| 33 06 607 | 9/1983 | Germany . | |
| 2176313 | 12/1986 | United Kingdom | 128/203.12 |

Primary Examiner—John G. Weiss
Assistant Examiner—V. Srivastava
Attorney, Agent, or Firm—McGlew and Tuttle

[57] ABSTRACT

A compact respirator, which is independent from a central air supply includes at least two gas supply lines, which lead to a gas mixer in the inspiration line. The gas lines are part of a mixing and metering unit, wherein one gas supply line has a compressor for ambient air and the at least one additional gas supply line has a metering unit for an auxiliary gas. Upstream of the gas mixer, there is a gas volume flow meter each in each of the gas supply lines. A pressure sensor is arranged in the inspiration line downstream of the gas mixer. The expiration line contains a discharge valve with a pressure sensor arranged upstream of the discharge valve. A central control unit is connected to the compressor, the metering unit, of which there is at least one, to the discharge valve, as well as to the pressure sensors. The gas volume flow meters, and control unit are provided for controlling the breathing pressure and the mixed gas composition after comparison of the signals measured by the pressure sensors as well as by means of the gas volume flow meters with predetermined set points.

14 Claims, 1 Drawing Sheet

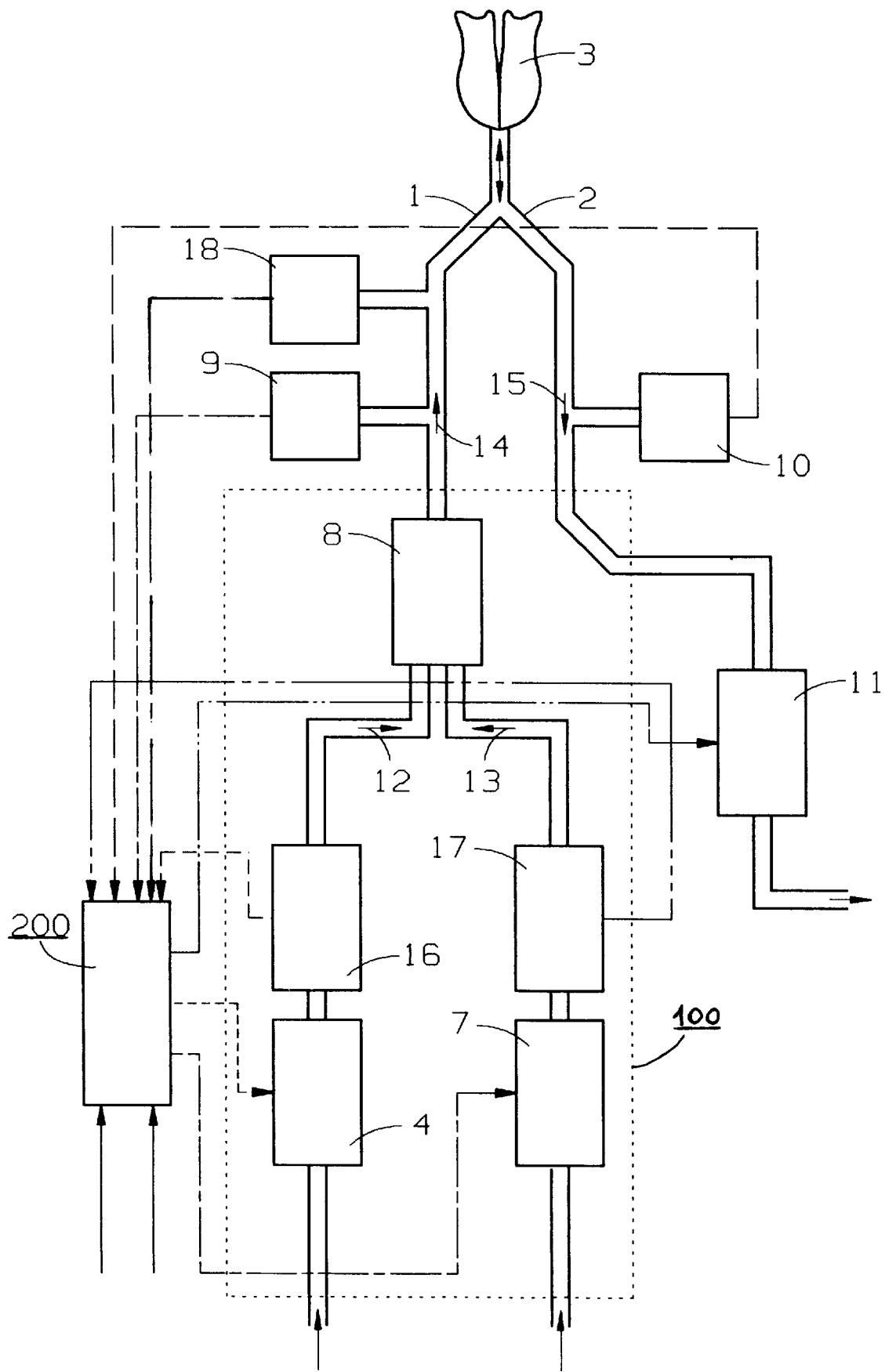

RESPIRATOR

FIELD OF THE INVENTION

The present invention pertains to a respirator with an inspiration line and an expiration line, which lead to the patient via a connection piece.

BACKGROUND OF THE INVENTION

Such respirators are used for the artificial respiration of patients, and modern respirators are able to more or less support the patient, depending on his current condition, as a function of his own breathing effort. Depending on the mechanical parameters of the lungs, the volume and flow resistance, a variable volume flow is fed, in general, to the patient in the form of an inspiration gas flow, and the percentage of oxygen can be additionally increased.

CA 2,036,184 A1 discloses a breathing system which has an oxygen supply from a pressurized tank and an air supply, as well as a mixing chamber for the two gases, in order to supply from it a downstream inspiration line belonging to it, which leads to the patient. The gas pressure in the supply line to the patient is regulated depending on the patient's measured breathing effort.

Depending on the particular country and on how the hospitals are equipped, the air and oxygen supply of the respirators is ensured either via central gas supply systems or via compressors for air and pressure cylinders for oxygen.

SUMMARY AND OBJECTS OF THE INVENTION

The primary object of the present invention is to provide a compact respirator which is supplied with ambient air and at the same time makes possible the addition of variable amounts of auxiliary gas from a reservoir under a pressure that is substantially higher than the ambient pressure.

According to the invention, a respirator with an inspiration line and an expiration line is provided which lead to the patient via a connection piece. At least two gas supply lines, which lead to a gas mixer in the inspiration line, are located in a mixing and metering unit. One of these gas supply lines has a compressor for drawing in and compressing ambient air. At least one additional line of the gas supply lines contains a metering unit for metering at least one auxiliary gas fed in, which is under a pressure that is substantially higher than the ambient pressure. One, gas volume flow meter is located in each of the gas supply lines, arranged upstream of the gas mixer. A pressure sensor is located in the inspiration line, arranged downstream of the gas mixer. The expiration line contains a discharge valve with a pressure sensor arranged upstream of the discharge valve. A central control unit is connected to the compressor, to the metering unit, to the discharge valve, as well as to the pressure sensors and to the gas volume flow meters. Means are provided to control the breathing pressure and the mixed gas composition after comparison of the signals measured by means of the pressure sensors as well as by means of the gas volume flow meters with predetermined set points.

The control unit preferably controls the mixed gas volume flow for reaching the preselected pressure level via the metering unit, the compressor and the discharge valve as a function of the values of the gas volume flow currently measured with the gas volume flow meters and of the values of the breathing pressure currently measured with the pressure sensors after comparison with preselected set points.

The compressor may be a radial compressor, a Roots blower, a side-channel blower, or a scroll compressor. A scroll compressor is preferably used. The compressor is preferably combined with a proportional valve arranged directly upstream or downstream of it.

The overall volume flow to the patient as well as the mixing ratio of air to one or more auxiliary gases are preferably set at the central control unit. The compressor and the metering unit are preferably controlled by the control unit after comparison with the volume flows actually measured by means of the gas volume flow meters before the gas mixer in order to reach the set points of the mixing ratio and of the overall volume flow.

The auxiliary gas, of which there is at least one, may be fed in from pressurized gas supply cylinders with pressure-reducing valves arranged downstream of them or from a central gas supply system, wherein the gas has an overpressure of about 2.5 to 6 bar. The system may have exactly two gas supply lines, and the auxiliary gas may be oxygen.

One essential advantage of the present invention is based on the fact that due to the independence from a central gas supply system, the respirators according to the present invention can be used in countries and hospitals without a corresponding infrastructure as well as in home therapy or in emergency medicine. The use of separate compressors arranged upstream of the respirator in countries in which hospitals do not have a functioning central gas supply is associated with numerous drawbacks, because limited service life as well as increased power consumption indirectly due to the high pressure must be accepted, besides the increased maintenance cost. It is especially disadvantageous that irregular or incorrect maintenance implies the risk of contamination of or damage to the downstream respirator, e.g., due to the penetration of oil, water or other residues.

The independence from central supply systems can be further increased in the case of electric power supply of the respirator according to the present invention from batteries or cells.

At the core of the present invention is the combination and the arrangement of the characterizing elements of the respirator according to the present invention, which are coordinated with one another such that the device is able to rapidly respond to the spontaneous breathing effort of the patient being subjected to artificial respiration. The rapidity of response of the valves and likewise that of the compressor is particularly important in this connection. The rapidity can be brought about by two alternative embodiments of the compressor. In the first and preferred embodiment, the compressor comprises a scroll housing, which is characterized in that it is able to rapidly deliver the necessary volume flows of air under sufficiently high pressure at a small size. The operating speeds, equaling 1,000 to a maximum of 3,000 rpm, are relatively low. The pressure ratio of the compressor is about 1:1.1. The rotating masses and consequently the mass moment of inertia are low, so that a highly dynamic response pattern is obtained concerning the air volume flow to be delivered. It is thus possible to reach the pneumatic response rates necessary in the case of spontaneous breathing with a scroll blower directly by accelerating the driving electric motor, and the necessary volume flow rates can be set by controlling the speed of the motor.

In an alternative embodiment of the compressor, it is also possible to select a more sluggish drive and to achieve the dynamics of the response by combination with a proportional valve. The proportional valve may be arranged directly downstream of the compressor and it is controlled, like the drive of the compressor, by a central control unit. The drawback of this second variant is that additional apparatus is needed in the form of a precision proportional valve. In addition, the compressor also must run during expiration because of its sluggish behavior in order to be always ready for delivering a volume of air that may possibly become spontaneously necessary. This leads to increased energy consumption. On the other hand, one advantage of this variant is that a comparatively simple compressor with motor can be used.

The present invention and its mode of operation will be explained by means of the only figure, which schematically shows the design of a respirator according to the present invention with its essential components.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a block diagram and schematic representation of the respirator according to the invention.

DESCRIPTION OF THE PREFERRED
EMBODIMENTS

Referring to the drawings in particular, the respirator includes a mixing and metering unit 100 and a central control unit 200 which are located in a housing (not shown) of the respirator according to the present invention. The inspiration line 1 leads from the respirator to the patient 3 via a connection piece and, via the expiration line 2, back to the line through which the expired gas is discharged into the environment via the expiration valve 11. The mixing and metering unit 100 has two gas supply lines 12, 13, which lead to a gas mixer 8 in the inspiration line 1. The gas supply line 12, which is the upper line in the figure, contains a compressor 4 for drawing in and compressing ambient air. The compressor 4 with a pressure ratio of about 1:1.1 may be designed as a highly dynamic, electrically driven blower unit, preferably as a scroll compressor, or, as an alternative, as a relatively sluggish compressor driven by an electric motor, combined with a dynamic proportional valve. The inlet pressure at the compressor 4, which is indicated by the arrow, is ambient pressure, which may vary within the range of variations predetermined by the weather, on the one hand, and by the geographic specifications of the site of use, on the other hand. Thus, external pressure variations in a pressure range of about 600 to 1,200 mbar are possible. Additional components, such as a bacteria filter and/or closing elements, which make no change in the general design and are also not shown, may optionally be provided before (upstream of) the compressor 4. The gas supply line 13, which is the lower line in the figure, contains a metering unit 7 for metering at least one auxiliary gas, which is fed in from a gas reservoir in the direction of the arrow under a pressure that is substantially higher than the ambient pressure, wherein this anxiliary gas is preferably oxygen. As an alternative, it would also be possible to provide a plurality of second gas supply lines 13 for different, medically indicated auxiliary gases, e.g., noble gases, such as xenon, or gaseous anesthetics, which would lead to the correspondingly adapted gas mixer 8. The auxiliary gas, preferably oxygen, is obtained, in general, from pressurized gas supply cylinders with pressure-reducing valves arranged downstream. Connection to a central gas supply system would also be possible, in principle. For worldwide use and for the different, technically possible pressure ranges of central gas supply systems, the auxiliary gas fed in has an overpressure of 2.5 to 6 bar. Both the gas supply line 12 for ambient air, which is the left line in the figure, and the at least one additional gas supply line 13, which is the right line in the figure, for the auxiliary gas or auxiliary gases, which is especially oxygen, contain a gas volume flow meter 16, 17 each before the gas mixer 8, which are connected to the control unit 200, so that the compressor 4 and the metering unit 7 can be set by the control unit 200 based on the preselected mixing ratio of air to auxiliary gas in order to obtain this preselected mixing ratio. A pressure sensor 9 and optionally a mixed gas sensor 18 are located behind the gas mixer 8 in the direction of flow, and both sensors are directly connected to the control unit 200. The mixed gas sensor 18 is dispensable, because the mixed gas composition can be determined or calculated by the central control unit 200 based on the measured values of the gas volume flow meters 16, 17. An additional pressure sensor 10, which is also connected to the control unit 200, is located before the discharge valve 11 in the expiration line 2.

The respirator according to the present invention operates in the following manner: Preselected values for the breathing pressure, the overall volume flow to the patient, as well as the mixing ratio of air to auxiliary gas(es) are set on the control unit 200. The control unit 200 acts on the compressor 4, the metering unit 7, and the discharge valve 11 as final control elements. The control unit 200 receives measured signals from the gas volume flow meters 16, 17, from the pressure sensors 9, 10, and optionally from the mixed gas sensor 18. As a result of the compressor action and the metering of the auxiliary gas, an inlet-side gas pressure of up to 80 to 100 mbar is reached in the device before the gas mixer 8. To reach this, the ambient air must be compressed to a pressure that is somewhat higher than the breathing pressure, and the pressure of the auxiliary gas must be released to a comparable pressure level via the metering unit 7 from a pressure level that is substantially higher than the ambient pressure. Finally, the air and the auxiliary gas or auxiliary gases are mixed in the gas mixer 8. The mode of operation of the device during respiration is as follows: In the case of spontaneous breathing, the breathing profile that the patient individually requires must be reached by the respirator. To do so, the current pressure level is determined by measuring the breathing pressure at the patient by means of the pressure sensor 10. This pressure is compared with the spontaneous breathing pressure set on the respirator. If the pressure is too low, a mixed gas volume flow, which increases until the required pressure level is reached, is additionally supplied via the metering unit 7 and the compressor 4 corresponding to the set mixing ratio of air to auxiliary gas(es). If, on the other hand, the measured pressure is too high, the volume flow is choked via the compressor 4 and the metering unit 7 until the desired pressure is reached. The discharge valve 11 is controlled depending on the pressure measured by the pressure sensor 9 in the inspiration line 1, and the expired air is released into the environment.

While specific embodiments of the invention have been shown and described in detail to illustrate the application of the principles of the invention, it will be understood that the invention may be embodied otherwise without departing from such principles.

What is claimed is:

1. A respirator with an inspiration line and an expiration line, which lead to a patient via a connection piece, the respirator comprising:

a gas mixer;

a mixing and/metering unit with two gas supply lines, which lead to said gas mixer in the inspiration line;

a compressor for drawing in and compressing ambient air, said compressor being provided connected to one of said gas supply lines;

a metering unit for metering at least one auxiliary gas fed in, which is under a pressure that is substantially higher than the ambient pressure, the metering unit being connected to another of said gas supply lines;

a first gas volume flow meter located in said one of said gas supply lines arranged upstream of said gas mixer;

a second gas volume flow meter located in said another of said gas supply lines arranged upstream of said gas mixer;

a first pressure sensor connected to said inspiration line arranged downstream of said gas mixer;

a discharge valve in the expiration line;

a second pressure sensor connected to said expiration line, arranged upstream of said discharge valve; and a central control unit connected to said compressor, said metering unit, said discharge valve, as well as to said pressure sensors and to said gas volume flow meters, said central control unit including control means for controlling the breathing pressure and the mixed gas composition after comparison of the signals measured, by means of said pressure sensors as well as said gas volume flow meters, with predetermined set points.

2. A respirator in accordance with claim 1, wherein said control unit controls the mixed gas volume flow for reaching a preselected pressure level via said metering unit, said compressor and said discharge valve as a function of the values of the gas volume flow currently measured with said gas volume flow meters and of the values of the breathing pressure currently measured with said pressure sensors after comparison with preselected set points.

3. A respirator in accordance with claim 1 wherein said compressor consists of a device selected from the group comprising: a radial compressor, a Roots blower, a side-channel blower, and a scroll compressor.

4. A respirator in accordance with claim 1 wherein said compressor is a scroll compressor.

5. A respirator in accordance with claim 1, wherein said compressor is combined with a proportional valve arranged directly upstream or downstream of said compressor.

6. A respirator in accordance with claim 1, wherein said central control unit sets an overall volume flow to the patient as well as a mixing ratio of air to one or more auxiliary gases, and said compressor and said metering unit are controlled by said control unit after comparison with the volume flows actually measured by said gas volume flow meters before said gas mixer in order to reach set points of the mixing ratio and of the overall volume flow.

7. A respirator in accordance with claim 1, wherein the auxiliary gas, of which there is at least one, is fed into said another of said gas supply lines from a pressurized gas supply cylinder with a pressure-reducing valve arranged downstream of said cylinder, wherein the gas has an overpressure of about 2.5 to 6 bar.

8. A respirator in accordance with claim 1, wherein the auxiliary gas, of which there is at least one, is fed into said another of said gas supply lines from a central gas supply system, wherein the gas has an overpressure.

9. A respirator in accordance with claim 1, wherein exactly two said gas supply lines are provided, and said auxiliary gas is oxygen.

10. A respirator comprising:

a connection piece leading to a patient;

an inspiration line connected to said connection piece;

an expiration line connected to said connection piece;

a gas mixer connected to said inspiration line, said gas mixer having first and second gas supply lines as inputs;

a first gas volume flow meter connected to said first gas supply line;

a second gas volume flow meter connected to said second gas supply line;

a compressor for drawing in and compressing ambient air, said compressor being connected to said first gas flow meter;

a metering unit for metering an auxiliary gas fed in under a pressure that is substantially higher than an ambient pressure, said metering unit being connected to said second gas flow meter;

a first pressure sensor connected to said inspiration line downstream of said gas mixer;

a discharge valve in the expiration line;

a second pressure sensor connected to said expiration line, and arranged upstream of said discharge valve;

a control unit connected to and controlling said compressor and said metering unit to provide a preselected ratio of air to auxiliary gas, said control unit receiving measured signals from said first and second gas volume flow meters, said control unit receiving measured signals from said first and second pressure sensors, said control unit controlling opening and closing of said discharge valve.

11. A respirator in accordance with claim 10, wherein:

said control unit measures a current pressure level from said second pressure sensor, said control unit compares said current pressure level with a predetermined breathing pressure, if said current pressure level is below said predetermined breathing pressure, said control unit controls said compressor and said metering unit to increase flow volume until said predetermined breathing pressure is measured.

12. A respirator in accordance with claim 10, wherein:

said control unit measures a current pressure level from said second pressure sensor, said control unit compares said current pressure level with a predetermined breathing pressure, if said current pressure level is above said predetermined breathing pressure, said control unit controls said compressor and said metering unit to decrease flow volume until said predetermined breathing pressure is measured.

13. A respirator in accordance with claim 11, wherein:

said control unit compares said current pressure level with said predetermined breathing pressure, and if said current pressure level is above said predetermined breathing pressure, said control unit controls said compressor and said metering unit to decrease flow volume until said predetermined breathing pressure is measured.

14. A respirator in accordance with claim 10, wherein:

said control unit measures a current pressure level from said first pressure sensor, said control unit controls said discharge valve depending on said current pressure level from said first pressure sensor.

* * * * *